(12) United States Patent
Gibson et al.

(10) Patent No.: US 6,426,340 B1
(45) Date of Patent: Jul. 30, 2002

(54) PREVENTION AND TREATMENT OF COLORECTAL CANCER BY 6-FLUOROURSODEOXYCHOLIC ACID (6-FUDCA)

(75) Inventors: Joyce Corey Gibson, Harding Township; Leonard Robert Capuano, Parsippany, both of NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/684,585

(22) Filed: Oct. 6, 2000

Related U.S. Application Data

(63) Continuation of application No. 09/180,785, filed as application No. PCT/EP97/02632 on May 22, 1997, now abandoned.
(60) Provisional application No. 60/018,202, filed on May 23, 1996.

(51) Int. Cl.$^7$ .............................................. A61K 31/56
(52) U.S. Cl. ....................................... 514/182
(58) Field of Search ......................................... 514/182

(56) References Cited

U.S. PATENT DOCUMENTS 5,175,320 A * 12/1992 Pellicciari et al. .......... 514/182
5,843,929 A    12/1998 Larson et al. ............... 514/182

FOREIGN PATENT DOCUMENTS

WO    WO 90 11526 A  * 10/1990 ................ 514/182

OTHER PUBLICATIONS

Roda et al., Gastroenterology, vol. 108, No. 4, pp. 1204–1214, 1995.*
H. Holubec et al., Gastroenterology, vol. 112, No. 4 Suppl., p. A579 (1997).
A.K. Batta et al., Hepatology, vol. 24, No. 4 Part 2, p. 372A, (1996).
A. Roda et al., Falk Symp. vol. 80, pp. 27–37 (1995).
A. Roda et al., Gastroenterology, vol. 108, No. 4, pp. 1204–1214 (1995).
D.M. Heuman, et al., Gastroenterology, vol. 110, No. 4 Suppl., p. A1210 (1996).
Earnest et al. Cancer Res., "Chemoprevention of Azoxymethane–induced Colonic Carcinogenesis by Supplemental Dietary Ursodeoxycholic Acid" pp. 5071–5074, (Oct. 1, 1994).

* cited by examiner

*Primary Examiner*—Jerome D. Goldberg
(74) *Attorney, Agent, or Firm*—Joseph J. Borovian

(57) ABSTRACT

Methods for the prevention and treatment of colorectal cancer are provided. Specifically, the method relates to the administration of an effective adenoma or microadenoma preventing amount of 6-fluoroursodeoxycholic acid (6-FUDCA) or a pharmaceutically acceptable salt or pharmaceutically acceptable conjugate thereof to a mammal in need of such treatment. The methods find general use in the prevention of the formation of secondary bile acids, the reduction of deoxycholic acid, and the protection against cytotoxic effects of other bioacids and carcinogens.

14 Claims, 3 Drawing Sheets

PREVENTION AND TREATMENT OF COLORECTAL CANCER BY 6-FLUOROURSODEOXYCHOLIC ACID (6-FUDCA)

This is a continuation of U.S. application Ser. No. 09/180,785, now abandoned having a 371 date of Nov. 16, 1998, which application is a 371 of International Application No. PCT/EP 97/02632, filed May 22, 1997 which claims benefit of Prov. No. 60/018,202 filed May 23, 1996.

FIELD OF THE INVENTION

The invention relates to the treatment and prevention of precancerous cell formation in the colon in those patients at risk for developing such precancerous cells. It also relates to preventing recurrence of such cell formation in those having been treated for cancer of the colon.

BACKGROUND OF THE INVENTION

Cancer of the colon is a common and deadly disease in the Western world. Genetic predisposition plays an important role, but exposure to substances that initiate and promote cancer is essential for a malignant tumor to develop. Bile acids have been implicated as important cancer-promoting agents.

In the normal colon mucosa, epithelial cells line crypt along the mucosal wall. Those epithelial cells which line the colon exposed surface and approximately the upper ⅔ of the crypt are normally non-proliferating, while those lining the lower ⅓ of the crypts are proliferating. As the proliferating cells migrate toward the upper portion of the crypt they transform and lose their proliferative ability. Ultimately the oldest cells are shed from the colon surface in the normal functioning of the colon. However, when the proliferating epithelial cells are induced to retain their proliferative capacity after reaching the upper ⅓ of the crypt, the normal process may go awry and microadenomas form. The proliferating cell, now at the surface of the colon continues to proliferate and a polyp develops.

Polyps may be either benign or cancerous. Some never become cancerous, but it is believed that adenomatous polyps are the main precursors of colon cancer and that about 90% of colon cancers develop from adenomatous polyps. Most adenomas do not continue to grow in size, but those that do are more likely to develop malignant changes. Therefore, reducing the number of adenomas and/or preventing their growth substantially reduces the number of potential colon cancers in the future.

Since subjects once treated for colon cancer have a much greater risk for developing further adenomas and cancers, potential adenoma prevention is extremely valuable in this population. The same may be said for close blood relatives of those treated for colon cancer, who may be at increased risk for adenoma and colon cancer development.

Bile acids have been implicated as important cancer promoting agents. In the normal sequence of events, bile acids are conjugated with taurine and glycine, making them more hydrophilic. It is these conjugated bile acids that are primarily involved in the digestion of fat. The bulk of these are reabsorbed in the final segment of the small bowel. However some of the conjugated bile acids are not absorbed and pass further down the GI tract.

Bacterial modification of the conjugated bile acids occurs in the lower intestine or colon. Two primary pathways are involved, deconjugation and dehydroxylation. Free bile acids are produced from the conjugate and removal of the 7-alpha hydroxyl group results in formation of secondary bile acids. Each of these steps changes the bile acid to a more lipophilic compound and to one which is more cytotoxic and more cancer promoting than the unmodified compound.

Normal fecal bile acids in healthy adults have been reported as:

| | | |
|---|---|---|
| Deoxycholic acid | 45%–55% | (more lipophilic) |
| Lithocholic acid | 30%–40% | (more lipophilic) |
| Cholic acid | 3%–5% | (more hydrophilic) |
| Chenodeoxycholic acid | 3%–5% | |
| Conjugated bile acids | <5% | (more hydrophilic) |
| Oxo bile acids | variable | |
| Unsaturated bile acids | <1% | |

The normal healthy control is believed to have a proper balance of bile acids. If the lipophilic/hydrophilic balance of the bile acid pool is significantly upset in the lipophilic direction, the bile acids may become toxic or harmful to the colonic epithelial cells. It is believed that as the lipophilic nature of the bile acid pool increases, the mucosal epithelial cells are more likely to be damaged by the presence of the secondary bile acids, especially deoxycholate. The damaged cells then begin the repair process which includes inducing cell proliferation. Repeated and frequent damage repeatedly induces proliferation and repair. The process of apoptosis or programmed cell death may also be affected. Research in rats has shown that excessive lipophilic bile acids in the colon can impair apoptosis and possibly increase the risk of forming adenomas and cancer. In addition, once the cell membrane has been compromised, agents which would not affect or which would have a difficult time affecting the colonic mucosal epithelial cells are more likely to have a significant impact.

There is therefore a need for a method for the treatment and prevention of colorectal cancer.

SUMMARY OF THE INVENTION

Figure 1:
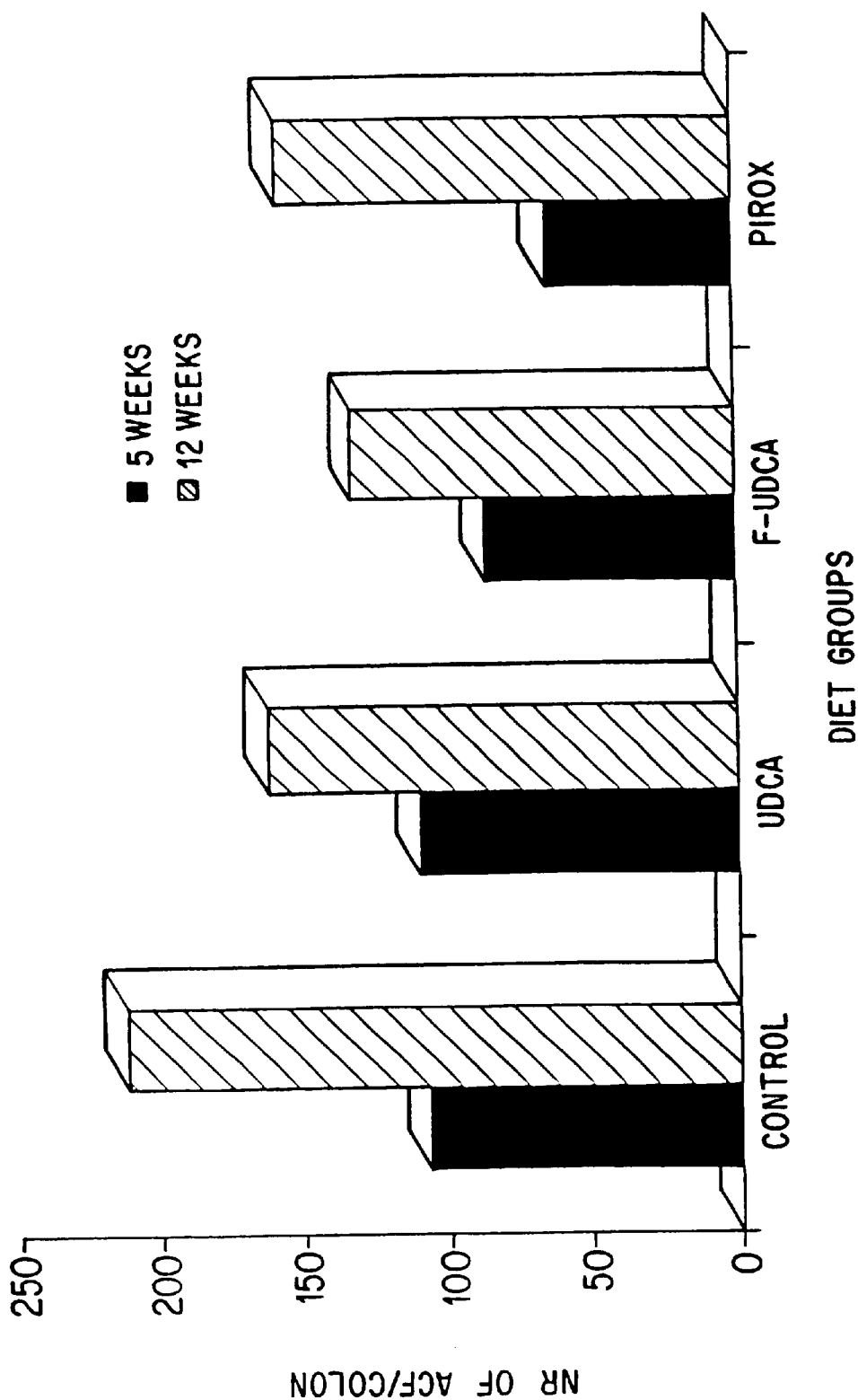
FIG. 1 contains the data from column 1 of Tables I and II.

The present invention relates to the use of an active agent selected from the group consisting of 6-fluoroursodeoxycholic acid (6-FUDCA), a pharmaceutically acceptable salt of 6-FUDCA, and a pharmaceutically acceptable conjugate of 6-FUDCA for the preparation of a pharmaceutical composition for use for the reduction of the incidence of or for the prevention of at least one of colonic adenomas or colonic microadenomas in a mammal at risk of developing such adenomas or microadenomas or for reducing fecal deoxycholic acid in a mammal. The present invention is drawn to the treatment or prevention of colorectal cancer. The method involves the administration of an effective adenoma or microadenoma preventing amount of 6-fluoroursodeoxycholic acid (6-FUDCA) or a pharmaceutically acceptable salt or pharmaceutically acceptable conjugate thereof to a mammal in need of such treatment. The method prevents the formation and/or growth of precursor lesions of cancer, protects colonic mucosal epithelial cells from the damaging effects of an overly lipophilic bile acid pool exposure, and lowers the risk of adenoma development in patients at risk for such development.

DETAILED DESCRIPTION OF THE INVENTION

Methods for the prevention and treatment of colorectal cancer are disclosed. The methods find general use in the prevention of the formation of secondary bile acids, the reduction of deoxycholic acid, and the protection against cytotoxic effects of other bioacids and carcinogens.

The method involves the administration of an effective amount of 6-fluoroursodeoxycholic acid (6-FUDCA) or a pharmaceutically acceptable salt or a pharmaceutically acceptable conjugate thereof to a mammal in need of such treatment. Such fluorinated bile acid derivatives are disclosed in U.S. Pat. Nos. 5,061,701 and 5,175,320, which disclosures are herein incorporated by reference. 6-FUDCA (chemical name: 3α, 7βdihydroxy-6α-fluoro-5β-cholanoic acid) is known as 6α-fluoroursodeoxycholic acid. 6-FUDCA is extremely resistant to bacterial dehydroxylation. The compound has a higher resistance to 7-dehydroxylation by intestinal bacterial flora, and accordingly a prolonged half-life as well as an increase in stability. 6-FUDCA is a hydrophilic, fluorinated derivative of ursodeoxycholic acid (UDCA). UDCA has been implicated in the chemoprevention of azoxymethane-induced colonic carcinogenesis. The present method is drawn to the use of 6-FUDCA the fluorinated derivative of UDCA for the prevention and treatment of colorectal cancer.

6-FUDCA has superior therapeutic properties when compared to UDCA. As compared with UDCA, the physico-chemical properties of 6-FUDCA demonstrate its improved cytoprotection. The water solubility of 6-FUDCA is higher than that of UDCA. The critical micellar concentration is slightly lower. The critical micellar pH of 6-FUDCA was also lower than that of UDCA. Additionally, the retention time on C-18 reverse phase HPLC was different for the two fluorinated diastereoisomers. That of the 6-α-epimer, which predominated, was slightly lower than UDCA, indicating increased hydrophilicity with respect to UDCA. The invention relates to the single isomers or diastereoisomers of 6-FUDCA and mixtures thereof.

6-FUDCA has greater absorption capacity and a reduced bacterial metabolism as compared to UDCA. Thus, 6-FUDCA is very important in treating or preventing colorectal cancer or any class of disease characterized by promotion or progression due to the effects of toxic bile acids.

While applicants are not bound to any particular mode of action set forth herein, it is believed that the therapeutic efficacy of 6-FUDCA relates to the ability of hydrophilic bile acid to displace hydrophobic and potentially toxic endogenous bile acids from the bile acid pool, and displacement of these hydrophobic bile acids from cellular membranes. In colorectal cancer, high levels of fecal hydrophobic bile acids (deoxycholic acid in particular) are associated clinically with risk of development of colorectal cancer. Treatment with 6-FUDCA effectively reduces fecal deoxycholic acid levels in parallel with reduced incidence of tumor development. 6-FUDCA shows improved solubility, reduced critical micellar pH, lack of bacterial metabolism, and enhances the enrichment of the bile acid pool. These properties, and the increased hydrophilicity of 6-FUDCA underlie the improved cytoprotection demonstrated by 6-FUDCA Pharmaceutically acceptable salts of 6-FUDCA include the alkali metal (preferably sodium and potassium) and alkaline earth metal (preferably calcium and magnesium) salts; most preferably sodium or potassium salts. Pharmaceutically acceptable conjugates of 6-FUDCA include conjugates thereof with glycine or taurine. Preferably, free 6-FUDCA is used in the present invention.

While any mammal may be treated with the present invention, the invention is primarily directed towards humans, farm animals, and pets; most preferably humans. For purposes of the present invention, the at risk population of one or more of the mammals to be treated includes those (1) having been diagnosed with colon cancer, colonic adenomas, and/or colonic microadenomas; and/or (2) having a close blood relative who has been diagnosed with colon cancer, colonic adenomas, and/or colonic microadenomas.

The compounds of the invention, for the envisaged therapeutical uses, are administered in the form of pharmaceutical compositions prepared accordingly to known techniques and excipients, as described e.g. in "Remington's Pharmaceutical Sciences Handbook," Hack Pub. Co., N.Y. USA.

An "effective amount" is an amount sufficient to reduce fecal deoxycholic acid levels and/or to reduce the incidence of colonic adenomas or colonic microadenomas in a mammal. The effective amount may vary from patient to patient depending on various factors including the patient's conditions, progression of disease, size or weight of the patient, etc. Generally, the effective amount of 6-FUDCA, its salts and its conjugates, is calculated on the amount of 6-FUDCA and is from about 1 mg/kg/day orally to about 30 mg/kg/day orally. Based upon the demonstrated metabolic stability of 6-FUDCA, efficacy may be achieved at a lower dose, preferably about 3 mg/kg/day to about 15 mg/kg/day; more preferably, about 5 mg/kg/day to about 8 mg/kg/day.

The preferred administration route is oral. The dosage may be in one or more divided doses. Typically, the daily dose is given in 1–4, preferably 2–3 divided doses. Typical doses for an adult human of about 60 kg is 300 mg of 6-FUDCA from one to four times, preferably 1–3 times, most preferably 2–3 times a day.

Examples of suitable pharmaceutical compositions comprise capsules, tablets, sugar-coated pills, syrups, granulates, solutions, vials. The compounds of the invention can also be administered by local profusion, before or after surgical operations in form of dispensable solutions or powders.

The compounds are prepared by methods which are known in the art. See, for example, U.S. Pat. Nos. 5,061,701 and 5,175,320.

When necessary or desirable, the active agent can be formulated with standard excipients and appropriate coating materials to obtain immediate release, controlled release or sustained release dosage forms. Such excipients include, but are not limited to: titanium dioxide, talc; starch; microcrystalline cellulose, microgranular cellulose, casein formaldehyde, colloidal silicon dioxide; lubricants such as magnesium stearate; colorants such as iron oxide; Eudragit coating materials, polyvinyl pyrrolidone, polyethyleneglycols, alumina, carboxymethylcellulose, and gelatin. Alternative specific formulations are disclosed in U.S. Pat. Nos. 3,859,437 and 4,263,272. Still other formulations will be readily apparent to those of ordinary skill in the pharmaceutical formulation art.

The following examples are offered by way of illustration and not by way of limitation.

Experimental

EXAMPLE I

Animals. Male albino Fischer-344 rats, initially weighing approximately 90–130 g, were used in these experiments.

All diets were obtained from Dyets, Inc. (Bethlehem, Pa.). On arrival, the animals were quarantined for 1 week and then divided into the following experimental groups:

Group 1—Standard AIN-76 diet only with no added agents (control group).

Group 2—AIN-76 diet plus UDCA 0.4%.

Group 3—AIN-76 diet plus 6-FUDCA 0.4%.

Group 4—AIN-76 diet plus piroxicam 75 ppm (included for a known positive drug control).

Protocol of Study. All rats were fed their assigned diets for 2 weeks, following which 10 rats in each group (except control group) were given s.c. injections of AOM (Sigma Chemical Co.; 15 mg/kg body weight) once a week for 2 weeks, while 5 rats received AOM vehicle. Control rats received AOM vehicle only. A week later (at week 3) rats received a second dose of carcinogen (AOM 15 mg/kg) while control rats received AOM vehicle. Each group was then maintained on their respective experimental diet for an additional 3 weeks. At this time, day 42, the rats were sacrificed; their colons were removed, opened, washed with normal saline, and examined macroscopically and microscopically for the presence of tumors. Aberrant crypts were quantified by direct microscopic counting of methylene blue stained whole colon. Stool specimens were removed from the colon at the time of termination, snap frozen, and maintained frozen for subsequent analysis of fecal bile acids.

Statistical Methods. The data were analyzed using the Aspin-Welch t-test, two sided. A value of $P<0.05$ was considered significant.

EXAMPLE II

The protocol for this Example was the same as that for Example I except that 12 rats were included in each AOM-treated group and 6 rats in each control group. Carcinogen was administered on Days 14 and 21. The rats were then continued on the diets containing the experimental drugs for an additional 10 weeks. The following tables set forth the data obtained in the study.

TABLE I

EFFECTS OF DIETARY SUPPLEMENTATION ON DEVELOPMENT OF ACF IN AOM RAT MODEL 5 WEEKS STUDY

| Diet Groups | N | Nr of ACF[a] | Multiplicity of[a] ACF | Total AC[a] count |
|---|---|---|---|---|
| CONTROL | 10 | 105.4 ± 26.8 | 3.0 ± 0.2 | 311.4 ± 82.3 |
| UDCA | 10 | 108.1 ± 34.7 | 2.0 ± 0.2[b] | 218.3 ± 73.3[b] |
| 6-FUDCA | 10 | 84.4 ± 16.3 | 1.9 ± 0.1[b] | 160.7 ± 34.6[b] |
| PIROXICAM | 10 | 62.9 ± 9.4[b] | 3.0 ± 0.2 | 190.1 ± 30.7[b] |

[a]Data = means ± Std. Dev.
[b]$P < 0.05$ compared to control

TABLE II

EFFECTS OF DIETARY SUPPLEMENTATION ON DEVELOPMENT OF ACF IN AOM RAT MODEL 12 WEEKS STUDY

| Diet Groups | N | Nr of ACF[a] | Multiplicity of[a] ACF | Total AC[a] count |
|---|---|---|---|---|
| CONTROL | 12 | 211.0 ± 38.7 | 3.4 ± 0.1 | 715.5 ± 134.2 |
| UDCA | 12 | 161.2 ± 37.8[b] | 2.8 ± 0.2[b] | 445.5 ± 87.4[b] |
| 6-FUDCA | 12 | 130.1 ± 35.5[b] | 2.7 ± 0.3[b] | 350.6 ± 87.3[b] |
| PIROXICAM | 12 | 156.3 ± 34.0[b] | 3.4 ± 0.3 | 625.3 ± 136.1[b] |

[a]Data = means ± Std. Dev.
[b]$P < 0.05$ compared to control

TABLE III

FECAL BILE ACIDS — % TOTAL

| GROUP | DC | α-MCA | HyoDC | UDCA | 6-FUDCA | Other |
|---|---|---|---|---|---|---|
| Control | 13.5 +/− 0.29 | 5.0 +/− 0.21 | 57.4 +/− 1.69 | 17.1 +/− 1.37 | 0 | 8.3 +/− 1.18 |
| UDCA | 1.1 +/− 0.14 | 4.7 +/− 0.55 | 4.4 +/− 0.79 | 65.5 +/− 1.18 | 0 | 24.3 +/− 0.42 |
| 6-FUDCA | 0.5 +/− 0.13 | 1.9 +/− 0.15 | 1.1 +/− 0.37 | 0.76 +/− 0.14 | 86.5 +/− 0.34 | 9.5 +/− 0.5 |
| PIROXICAM | 10.0 +/− 0.82 | 6.6 +/− 1.38 | 44.9 +/− 4.89 | 16.6 +/− 2.10 | 0 | 22.4 +/− 4.3 |

Figure 2:
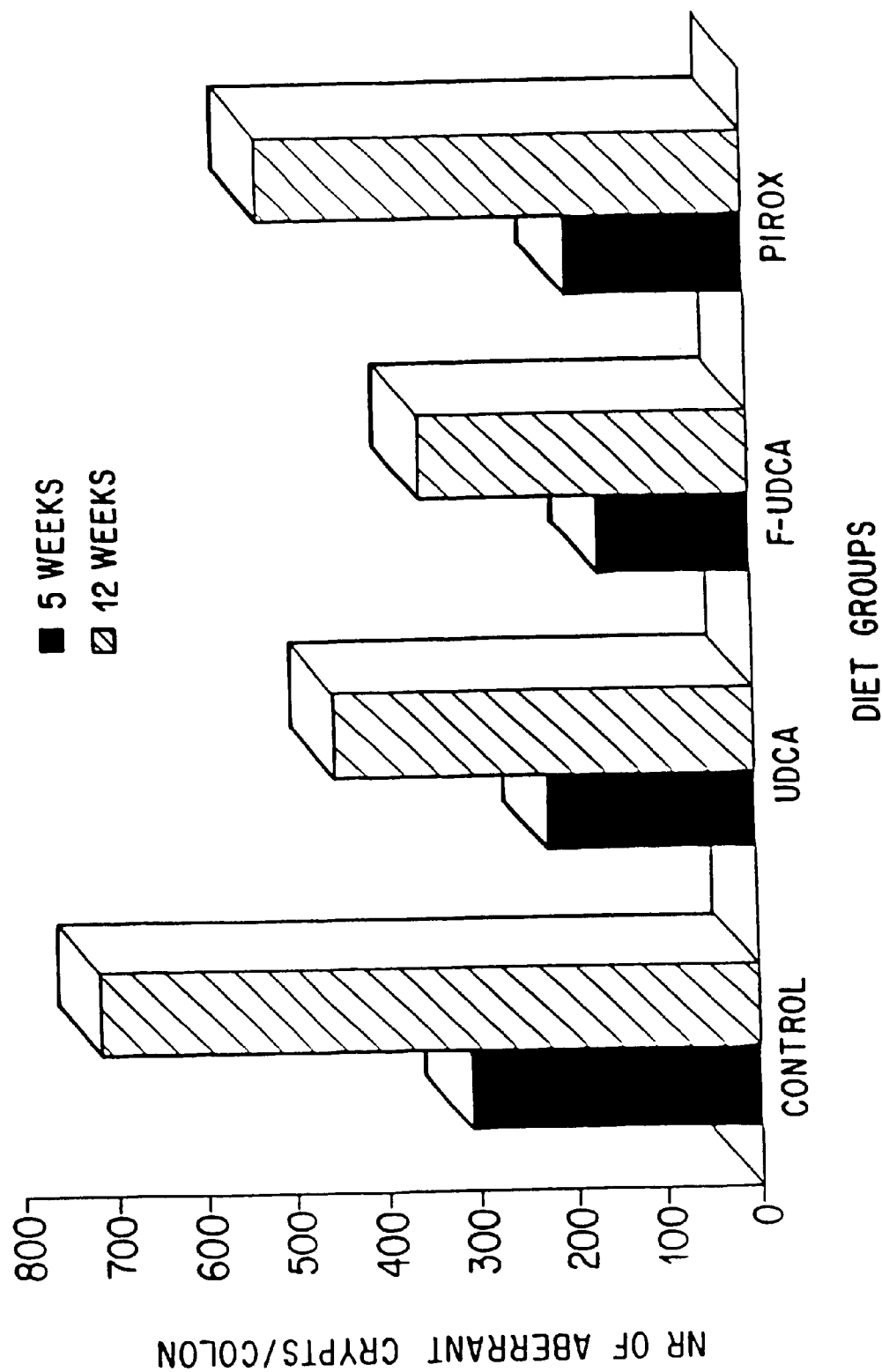
FIG. 2 provides the data from column III of Tables I and II.

Mean +/− SEM (n = 10)
DC = deoxycholic, MCA = murocholic, HyoDC = hyodeoxycholic
UDCA = ursodeoxycholic, 6-FUDCA = 6-fluoroursodeoxycholic The first two Tables contain the data and statistical analysis of the data. The data from column 1 of Tables I and II are shown in FIG. 1. FIG. 2 provides the data from column III of Tables I and II.

Figure 3:
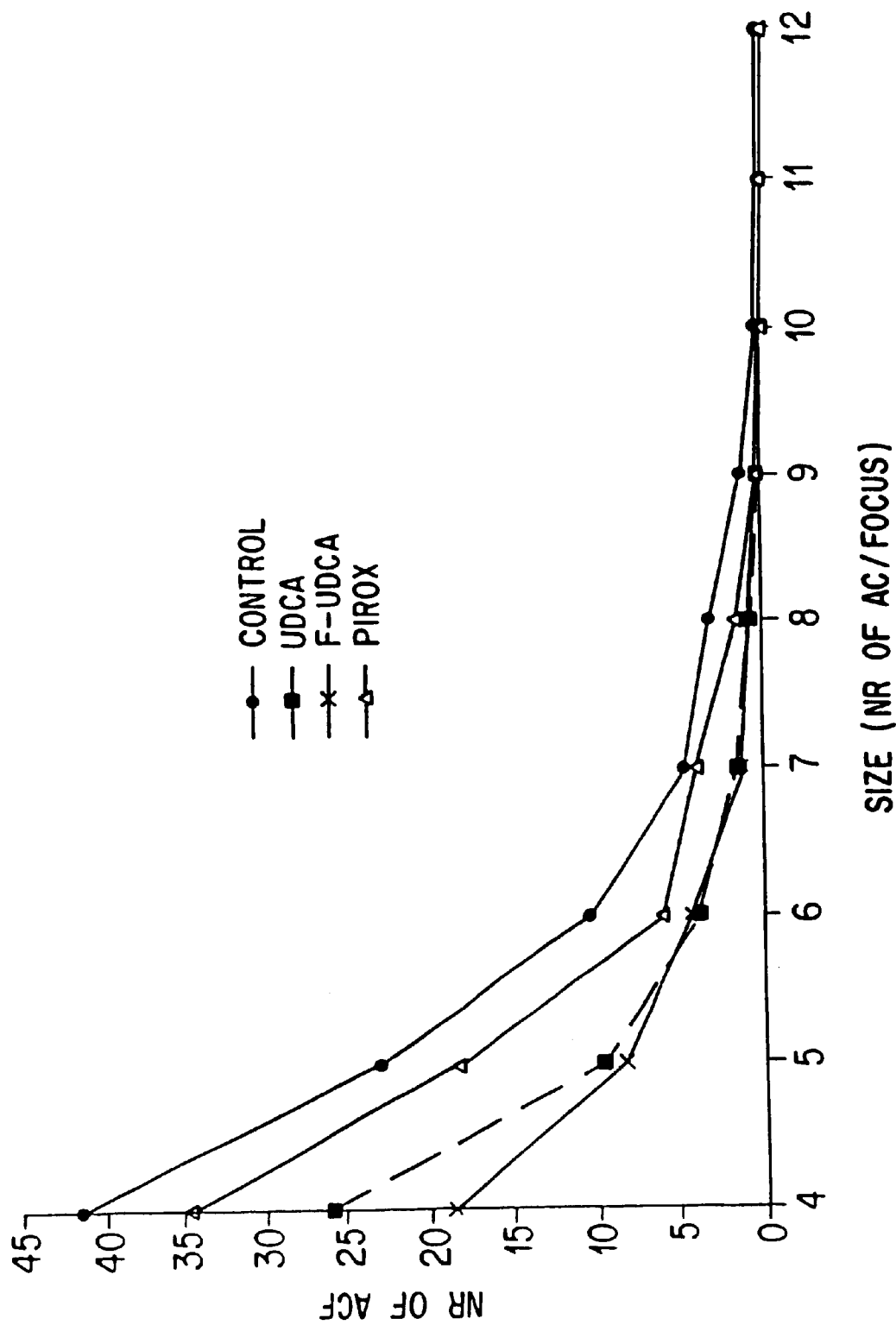
FIG. 3 provides data which demonstrates that the rats treated with 6-FUDCA had aberrant crypt foci with fewer aberrant crypts.

As is emphasized in FIG. 3, the rats treated with 6-FUDCA had aberrant crypt foci with fewer aberrant crypts. This is important because it is the aberrant crypt foci with high multiplicity of aberrant crypts which are more apt to develop into neoplastic lesions.

Because of the metabolic stability of 6-FUDCA and its ability to accumulate in the bile to a greater extent then does UDCA, the minimum effective dose of 6-FUDCA is predicted to be lower than that of UDCA.

Table III shows that 6-FUDCA is not metabolized by bacteria in the gut. Thus, potentially toxic bile acids, deoxycholic acid and lithocholic acid do not accumulate. Table III provides an analysis of fecal bile acid levels in the experiment. It shows that 6-FUDCA accumulates to a greater degree then does UDCA (86.5% in the 6-FUDCA group versus 65.5% in the UDCA group). In addition, less DC and hyoDC are seen in the feces of 6-FUDCA rats than in UDCA rats. Therefore, 6-FUDCA enriches rat bile with therapeutic bile acid to a greater extent then can UDCA. Furthermore, 6-FUDCA reduces the formation of bile acids which are potentially toxic to the colonic mucosa.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for the reduction of the incidence of, or for the prevention of, at least one of colonic adenomas or colonic microadenomas in a mammal in need thereof comprising administering to said mammal an effective adenoma or microadenoma preventive or incidence reducing amount of an active agent selected from the group consisting of 6-fluoroursodeoxycholic acid (6-FUDCA), a pharmaceutically acceptable salt of 6-FUDCA, a pharmaceutically acceptable conjugate of 6-FUDCA with glycine, and a pharmaceutically acceptable conjugate of 6-FUDCA with taurine.

2. The method of claim 1 wherein said mammal is selected from farm animals, household pets, and humans.

3. The method of claim 2 wherein said mammal is a human.

4. The method of claim 1 wherein said active agent is free 6-FUDCA.

5. The method of claim 1 wherein said effective amount is from about 1 mg/kg/day to about 30 mg/kg/day orally calculated on the base of free 6-FUDCA.

6. The method of claim 1 wherein said effective amount is from about 5 mg/kg/day to about 8 mg/kg/day.

7. The method of claim 1 wherein said daily dose of said active agent is administered in from 1 to 4 divided doses.

8. The method of claim 1 wherein said daily dose of said active agent is administered in from 2 to 3 divided doses.

9. The method of claim 1 wherein said mammal at risk of developing colonic adenomas and/or colonic microadenomas is selected from those mammals which (a) have been diagnosed with at least one of colon cancer, colonic adenomas, and colonic microadenomas; and/or (b) have a close blood relative diagnosed with at least one of colon cancer, colonic adenomas, colonic microadenomas, and colonic polyps.

10. A method for reducing fecal deoxycholic acid in a mammal in need thereof comprising administering to said mammal a fecal deoxycholic acid reducing effective amount of an active agent selected from the group consisting of 6-FUDCA, a pharmaceutical acceptable salt of 6-FUDCA, a pharmaceutically acceptable conjugate of 6-FUDCA with glycine, and a pharmaceutically acceptable conjugate of 6-FUDCA with taurine.

11. The method of claim 10 wherein said effective amount is from about 1 mg/kg/day to about 30 mg/kg/day orally calculated on the basis of free 6-FUDCA.

12. The method of claim 10 wherein said effective amount is from about 5 mg/kg/day to about 8 mg/kg/day.

13. The method of claim 10 wherein said daily dose of said active agent is administered in from 1 to 4 divided doses.

14. The method of claim 10 wherein said daily dose of said active agent is administered in from 2 to 3 divided doses.

* * * * *